(12) United States Patent
Urie

(10) Patent No.: US 9,687,632 B2
(45) Date of Patent: Jun. 27, 2017

(54) CATHETER

(75) Inventor: Robert Graham Urie, High Wycombe (GB)

(73) Assignee: Mediplus Limited, Bucks (GB)

( * ) Notice: Subject to any disclaimer, the term of this patent is extended or adjusted under 35 U.S.C. 154(b) by 318 days.

(21) Appl. No.: 13/386,061

(22) PCT Filed: Jun. 23, 2010

(86) PCT No.: PCT/GB2010/001235
§ 371 (c)(1),
(2), (4) Date: Jan. 20, 2012

(87) PCT Pub. No.: WO2011/010079
PCT Pub. Date: Jan. 27, 2011

(65) Prior Publication Data
US 2012/0271280 A1    Oct. 25, 2012

(30) Foreign Application Priority Data

Jul. 23, 2009 (GB) .................................. 0912797.8

(51) Int. Cl.
*A61M 27/00* (2006.01)
*A61M 25/04* (2006.01)
A61M 25/00 (2006.01)

(52) U.S. Cl.
CPC ......... *A61M 25/04* (2013.01); *A61M 25/0054* (2013.01); *A61M 25/0074* (2013.01);
(Continued)

(58) Field of Classification Search
CPC .. A61M 2025/0004; A61M 2025/0006; A61M 25/0075; A61M 25/0074;
(Continued)

(56) References Cited

U.S. PATENT DOCUMENTS 3,053,257 A * 9/1962 Birtwell ............ A61M 25/0017
604/916
3,108,595 A 10/1963 Overment
(Continued)

FOREIGN PATENT DOCUMENTS

EP  0 368 473 A2  5/1990
WO  95/30449 A1  11/1995
(Continued)

OTHER PUBLICATIONS

International Search Report of corresponding International Application No. PCT/GB2010/001235, dated May 3, 2011.

*Primary Examiner* — Leslie Deak
*Assistant Examiner* — Kai Weng
(74) *Attorney, Agent, or Firm* — Blank Rome LLP

(57) ABSTRACT

A catheter comprising an inner sleeve and an outer sleeve surrounding the inner sleeve, the inner and the outer sleeves being longitudinally displaceable relative to one another to enable the catheter to move from an open state to a closed state, each sleeve having a distal portion and a proximal portion, the catheter further comprising a retainer which is open in the open state, and closed in the closed state, the catheter further comprising a lock mechanism comprising lock formed in a lock portion of the catheter for locking the catheter in the open state, and a releaser for releasing the lock, the releaser being adapted to remove at least a part of the lock portion from the catheter.

11 Claims, 7 Drawing Sheets

Figure 4:
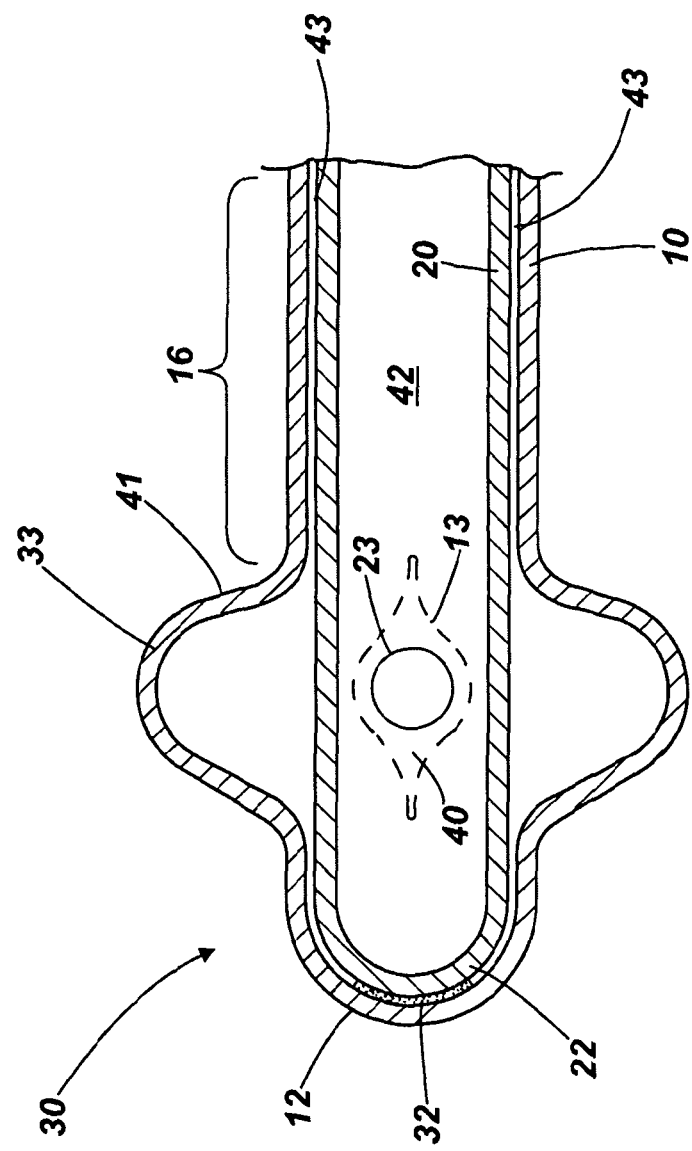

(52) U.S. Cl.
CPC . *A61M 25/0075* (2013.01); *A61M 2025/0004* (2013.01); *A61M 2025/0006* (2013.01)

(58) Field of Classification Search
CPC .............. A61M 25/00; A61M 25/0054; A61M 25/0067; A61M 25/007; A61M 2025/0067; A61M 2025/0074; A61M 2025/0075; A61M 2025/0079; A61M 2039/22
USPC ................................ 604/544, 105, 107, 537
See application file for complete search history.

(56) References Cited

U.S. PATENT DOCUMENTS

| | | | |
|---|---|---|---|
| 3,651,807 A * | 3/1972 | Huggins | A61M 25/065 604/161 |
| 4,608,965 A | 9/1986 | Anspach, Jr. et al. | |
| 5,312,337 A * | 5/1994 | Flaherty et al. | 285/278 |
| 2001/0049494 A1 | 12/2001 | Liu | |
| 2004/0243104 A1 | 12/2004 | Seddon | |
| 2008/0154176 A1* | 6/2008 | Van Ingelgem et al. | 604/18 |
| 2008/0228174 A1* | 9/2008 | Ibrahim | A61M 25/02 604/541 |
| 2008/0319456 A1* | 12/2008 | Hart | 606/142 |

FOREIGN PATENT DOCUMENTS

| WO | WO 95/30449 A1 | 11/1995 |
|---|---|---|
| WO | 2004/045696 A1 | 6/2004 |
| WO | WO 2004/045696 A1 | 6/2004 |
| WO | 2005/025645 A2 | 3/2005 |
| WO | WO 2005/025645 A2 | 3/2005 |
| WO | WO 2006/052281 A2 | 5/2006 |

* cited by examiner

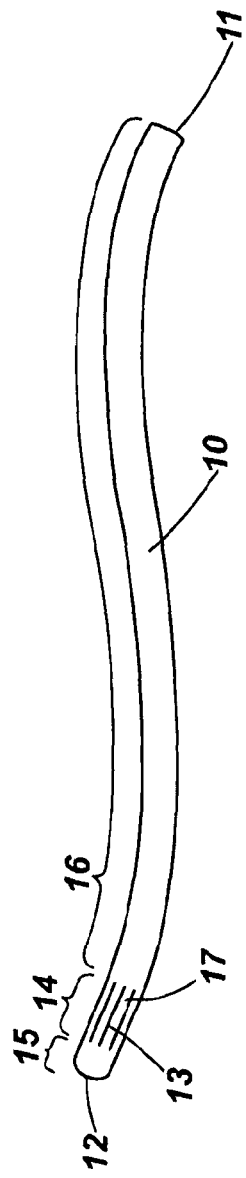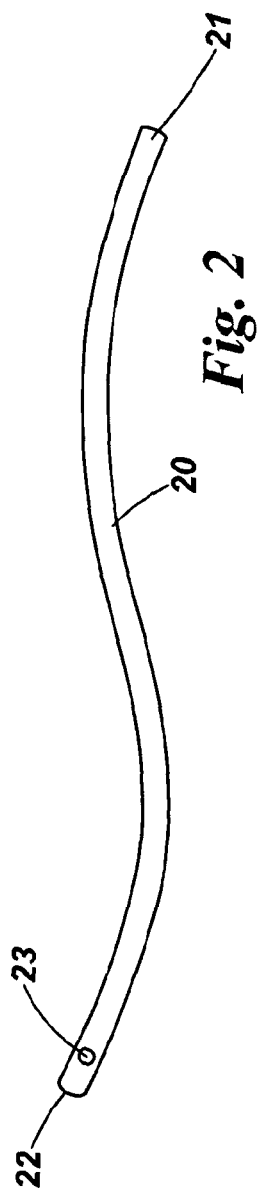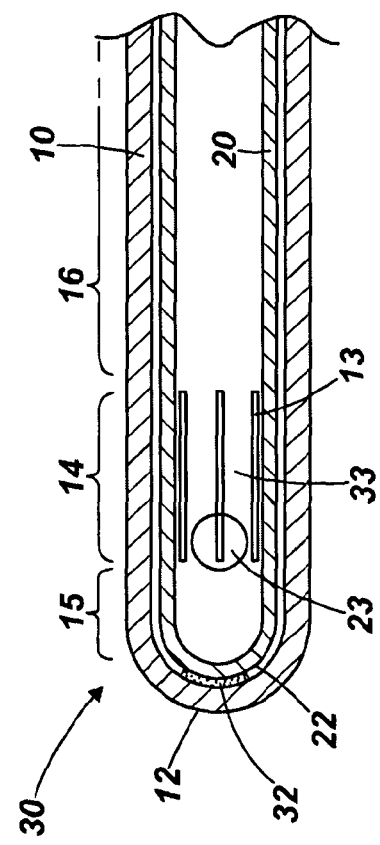

ns for catheter apparatus.
CATHETER

This application is a national phase of International Application No. PCT/GB2010/001235 filed Jun. 23, 2010, and published in the English language as WO 2011/010079 on Jan. 27, 2011.

The present invention relates to catheters and lock mechanisms for catheter apparatus.

Conventional urinary drainage catheters generally comprise a tube having a distal end which is inserted into a patient's body, a proximal end which remains outside the patient's body, and at least one lumen extending through the tube for the passage of urine out of the body. The distal end is introduced into the bladder via the urethra or suprapubically, and extends a short distance into the bladder where it is maintained in position by a suitable retention mechanism.

There are a number of conventional retention mechanisms available in the art, one of which provides an inflatable balloon at the distal end of the catheter, which is inflated after being introduced into the bladder via the urethra. The inflated balloon engages with the neck of the bladder, thereby preventing the catheter from inadvertently being withdrawn from the bladder.

Other retention mechanisms make use of a flexible, resilient wing structure at the distal end of the catheter, in which the wings can be compressed (closed) umbrella-like to be aligned with the catheter for introduction through the urethra. Once the wing structure reaches the bladder, it is allowed to spring back into an appropriate expanded or 'open' form to prevent egress of the catheter from the bladder.

Another retention mechanism is described in International patent application PCT/GB2003/005022, in the name of Mediplus Limited. In this type of catheter the retention mechanism is based on a deformable zone of an outer sleeve of the catheter, the outer sleeve surrounding an inner sleeve which are both fixed together at the distal ends of the sleeves. The inner sleeve is lubricated so as to allow relative longitudinal displacement between the outer and inner sleeves of the catheter. The deformable zone comprises a plurality of elongate slits which are opened by deformation of the zone via a compression mechanism, which is applied after introduction of the distal end of the catheter into the bladder.

The deformation of the zone causes the zone walls to bulge or splay outwardly, whereby the splayed walls engage with the neck of the bladder, preventing egress of the distal end of the catheter past the bladder neck.

The open elongate slits are generally longitudinally aligned with an aperture in the inner sleeve of the catheter, which allows urine in the bladder to drain away by means of a lumen inside the inner sleeve, into a collection receptacle, such as a urine drainage bag.

The catheter of the above application also provides a mechanism for locking the inner and outer sleeves in a particular longitudinal displacement, corresponding to the open slit configuration. Locking mechanisms are necessary when the walls of the outer sleeve are resilient such that there is a tendency for them to try to close the slits that have been opened up in the open configuration. The necessity for any such locking mechanism may also depend upon the frictional resistance to the relative longitudinal movement of the inner and outer sleeves.

A known locking mechanism for locking the inner and outer sleeves comprises a circlip, or spring clip, clipped onto the proximal end of the inner sleeve which emerges from the proximal end of the outer sleeve. The clip extends around the inner sleeve in a tight frictional engagement that resists any longitudinal movement of the clip along the inner sleeve. The clip bears against the end wall of the outer sleeve at the proximal end, by way of an intervening olive, which has a tapered leading edge to engage with, and slightly under, the proximal end of the outer sleeve.

By appropriate positioning of the clip along the proximal end portion of the inner sleeve, the degree of longitudinal compression of the outer sleeve may be controlled, such that the outer sleeve can be locked in a position corresponding to the open configuration.

However, a potential disadvantage of a clip based locking mechanism is that the outer sleeve must be held in a compressed position (typically corresponding to the open configuration) while attempting to engage the clip with the inner sleeve.

Moreover, lateral adjustments in the position of the clip may also be difficult to accomplish where tight frictional engagement of the clip with the inner sleeve could prevent easy movement of the clip along the inner sleeve.

To ensure that the clinician achieves the correct degree of compression of the deformable zone they may conventionally rely on visual indicators located on the inner sleeve, in order to assess the extent of the relative longitudinal displacement between the inner and outer sleeves.

UK patent application no. 0416981.9 in the name of Mediplus Limited relates to a proximal end adapter for a catheter of the type described above and comprising an inner sleeve and an outer sleeve.

Hereinafter, it is to be understood that all references to 'catheter' are to be taken as referring to a catheter having two components that are to be longitudinally displaceable relative to one another, e.g. the inner and outer sleeves of a catheter as described above, in which relative longitudinal displacement of the inner and outer sleeves enables the catheter to move between an open state and a closed state.

According to a first aspect of the present invention there is provided a catheter comprising an inner sleeve and an outer sleeve surrounding the inner sleeve, the inner and the outer sleeves being longitudinally displaceable relative to one another to enable the catheter to move from an open state to a closed state, each sleeve having a distal portion and a proximal portion, the catheter further comprising a retainer which is open in the open state, and closed in the closed state and a lock mechanism comprising a lock for locking the catheter in the open state, and a releaser for releasing the lock, the releaser being adapted to remove at least a part of the lock from the catheter.

By means of the invention therefore at least part of the lock is removable by the releaser. This results in the lock being released thus allowing the catheter to return to the closed state, which in turns allows the catheter to be removed from a patient's body.

Preferably, the lock mechanism is positioned in the proximal portion of the catheter.

In some embodiments of the invention, once the or a part of the lock has been removed from the catheter, it is not possible to reattach the lock or part of the lock to the catheter. Such embodiments in the invention generally comprise disposable catheters that are designed to be used only once before being disposed of.

The releaser may comprise a frangible portion. The frangible portion may be in a form of an area, or line, of weakness which allows at least a part of the lock to be removed by causing the frangible portion to break along the area or line of weakness.

The releaser may comprise a tab extending from the lock portion and connected to the frangible portion.

In use, the tab may be pulled to cause the frangible portion to break away from the remainder of the lock.

The releaser may comprise one or more handles. Force applied to the handles may cause the frangible portion to break away from the remainder of the lock.

The lock may comprise a first lock component and a second lock component, the first and second lock components being engageable with one another.

The first and second lock components are positioned such that when the outer sleeve is displaced longitudinally to move the catheter into the open state, the first and second lock components engage with one another such that the catheter is held in the open state.

By removing the first lock component or a part of the first lock component, the second lock component can no longer engage with the first lock component, and the lock is released allowing the outer sleeve to return to its initial position in which the catheter is in its closed state. As mentioned above, this causes the catheter to return to its closed position, allowing the catheter then to be removed from a patient's body.

The first lock component may be formed on the outer sleeve, and the second lock component may be formed on the inner sleeve.

In such embodiments, the releaser is adapted remove at least a portion of the first lock component. The releaser may be located on, attachable to, or form part of the outer sleeve.

The first and second lock components may be formed integrally with the outer and inner sleeves respectively.

Alternatively, the first and second lock components may be formed separately from the outer and inner sleeves respectively and may be mounted on a respective sleeve.

In such embodiments, the first lock component may be engageable with the outer sleeve, and the second lock component may be engageable with the inner sleeve.

Both the first and second lock components may be engageable with a respective sleeve by means of portions such as ridges or grooves which are engageable with corresponding portions on the respective sleeve. Alternatively, each of the first and second lock components may be shaped such that when the component is positioned on a respective sleeve, an interference fit is created between the lock component and the respective sleeve.

Each lock component may comprise ridges or grooves extending circumferentially around a respective lock component, which ridges or grooves are engageable with corresponding grooves or ridges respectively formed on an outer surface of the inner or outer sleeves respectively.

The first and second lock components may each be formed as a single component. Alternatively the first lock component and/or the second lock component may each comprise more than one component.

The first lock component may comprise a first lock portion adapted to engage with the outer sleeve, and a second lock portion adapted to engage with the first lock portion.

The first lock portion may be in the form of an adaptor which is mounted on the outer sleeve and engageable with the first lock component.

The second lock portion may be engageable with the second lock component.

Alternatively, or in addition, the second lock portion may comprise the releaser. In other words, the releaser takes the form of the second lock portion of the first lock component. In such an embodiment, the releaser is engageable with both the second lock component which is formed on, or attachable to the inner sleeve, and the first lock portion of the first lock component which is formed on, or attachable to the outer sleeve. This means that when the first and second lock components are engaged with one another the first and second sleeves are held in position holding the catheter in the open state.

The first lock portion may comprise one or more recesses, and the second lock portion may comprise corresponding one or more engagement portions shaped to be received in a respective recess to thereby engage the first and second lock portions together.

In embodiments of the invention in which the first and second lock components are formed integrally with the outer and inner sleeves respectively, the first lock component may comprise a recess in the outer sleeve, and the second lock component may be shaped to be receivable within the recess.

The recess may extend from an inner surface of the outer sleeve inwardly towards the outer surface of the outer sleeve.

In this embodiment, the second lock component may be in the form of a protuberance, extending outwardly from an outer surface of the inner sleeve.

In other embodiments, a protuberance may be formed on the outer sleeve and extend inwardly from an inner surface of the outer sleeve to be engageable with a recess formed on the inner sleeve and extending from an outer surface of the inner sleeve.

The catheter may comprise a plurality of recesses spaced apart circumferentially and extending outwardly from the inner surface of the outer sleeve, and the second lock component may comprise a corresponding plurality of protuberances spaced apart circumferentially and extending outwardly from an outer surface of the inner sleeve circumferentially around the sleeve.

Alternatively, the plurality of recesses may be formed on the inner sleeve and may extend inwardly from an inner surface of the inner sleeve, and a plurality of protuberances may be formed on the outer sleeve and extend inwardly from the inner surface of the outer sleeve.

Alternatively, the first lock component may comprise a groove extending substantially circumferentially around an inner surface of the outer sleeve, and the second lock component may comprise a ridge extending substantially circumferentially around the inner sleeve and extending from an outer surface thereof.

The relative positions of the groove and the ridge are such that when the outer sleeve is displaced longitudinally such that the catheter assumes its open state, the ridge will engage with the groove. This means that the catheter will be locked in its open state.

In some embodiments, the first lock component may comprise a ridge extending substantially circumferentially from an inner surface of the outer sleeve, and the second lock component may comprises a groove extending substantially circumferentially around an outer surface of the inner sleeve.

The second lock component may comprise a cone component, which cone component may be formed integrally, or separately, to the inner sleeve. The cone component may be substantially conical, or frusto-conical in shape.

The outer sleeve may comprise an extension sleeve extending from the proximal portion of the outer sleeve. In such embodiments, the first lock component may be formed in, or on, the sleeve extension.

This means that if a force is applied to the protuberance, the sleeve extension will either break away from the outer sleeve, or will break apart causing the protuberance to become detached from the outer sleeve. This causes the or a part of the lock portion portion to be removed from the remainder of the catheter.

In some embodiments, the lock portion of the catheter may be reattached to the catheter in order that the catheter may be used again. In such embodiments, the releaser may comprise, for example, a zip fastener for allowing removal and reattachment of the lock portion to the catheter.

The retainer may take any suitable form and may, for example, be in the form of a resilient wing structure at the distal portion of the catheter. Alternatively, the retainer may comprise a deformable zone formed in the outer sleeve, the inner and outer sleeves being fixed together at or close to the deformable zone, the deformable zone extending in a direction substantially transversely to the catheter when the outer sleeve is compressed longitudinally to the catheter.

The deformable zone may be located at the distal portion of the catheter.

According to a second aspect of the present invention there is provided a lock mechanism for a catheter according to the first aspect of the present invention.

According to a third aspect of the present invention there is provided a method of deploying a catheter according to the first aspect of the invention, the method comprising the steps of:
  inserting the catheter into a patient's body until the distal portion is positioned within the bladder of the patient;
  longitudinally displacing the outer sleeve relative to the inner sleeve such that the retainer is deployed to its expanded state;
  locking the outer and inner sleeves in their relative longitudinal positions to maintain the catheter in the open state;
  after use of the catheter removing at least a part of the lock portion from the catheter in order to release the lock;
  removing the catheter from the patient's body.

Figure 5:
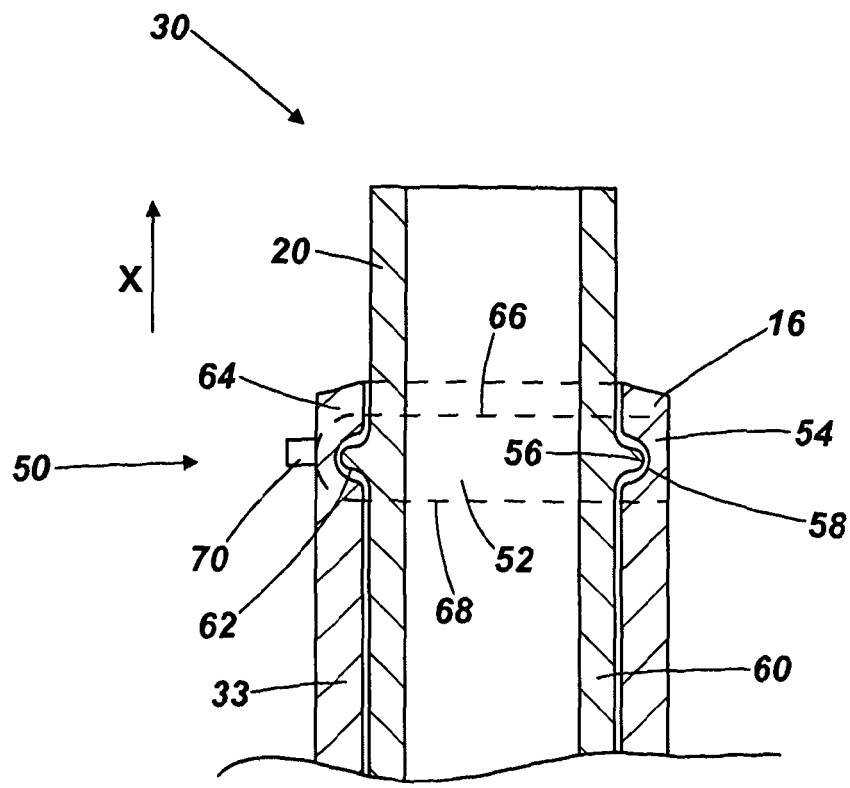
Figure 6:
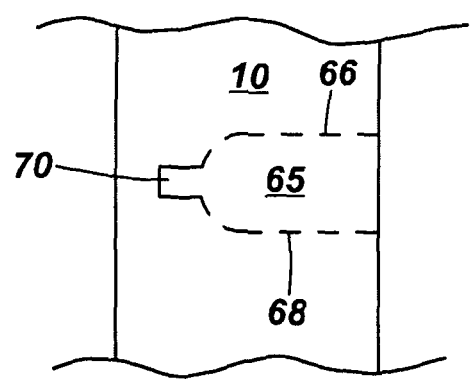
Figure 7:
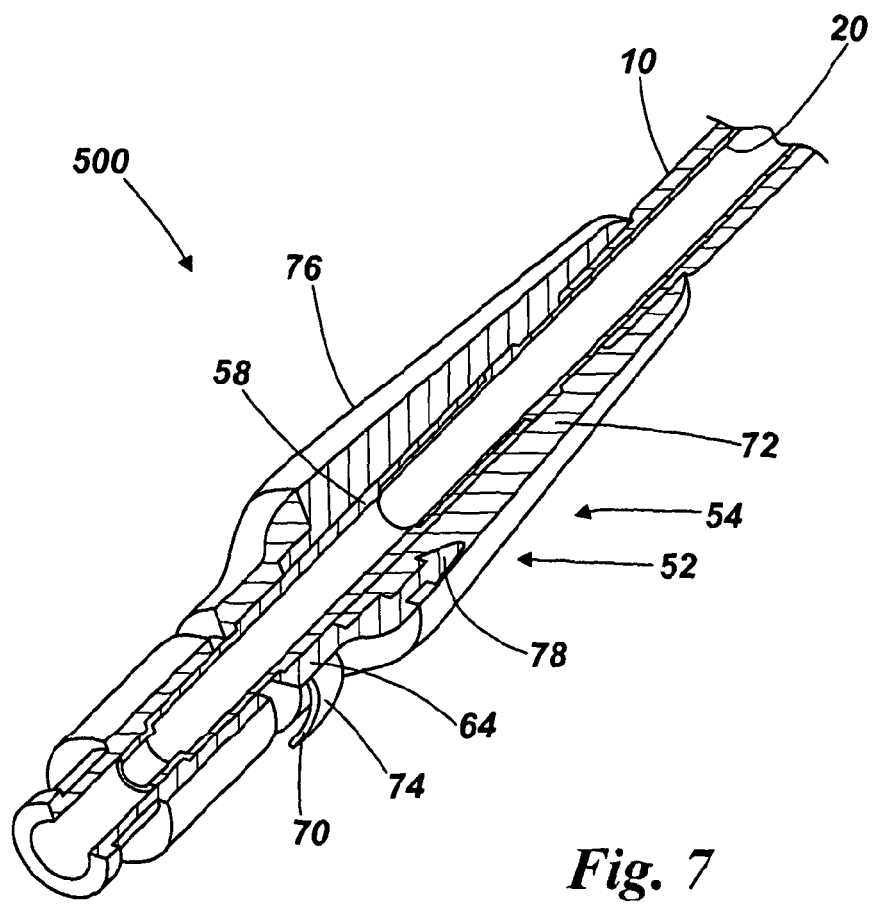
Figure 8:
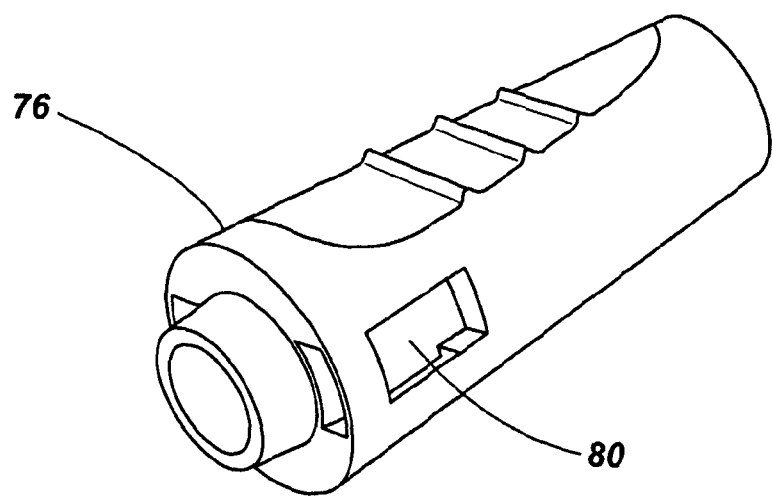
Figure 9:
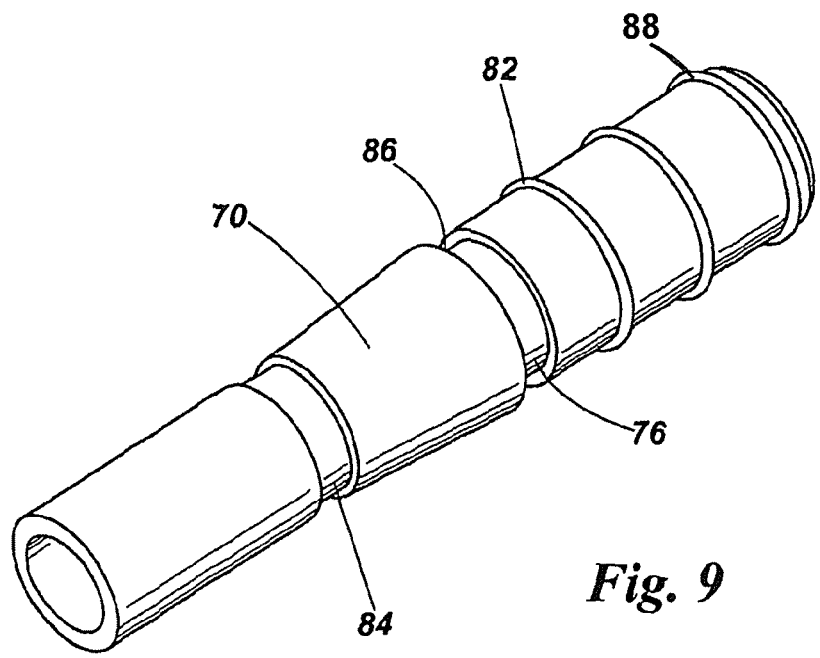
Figure 10:
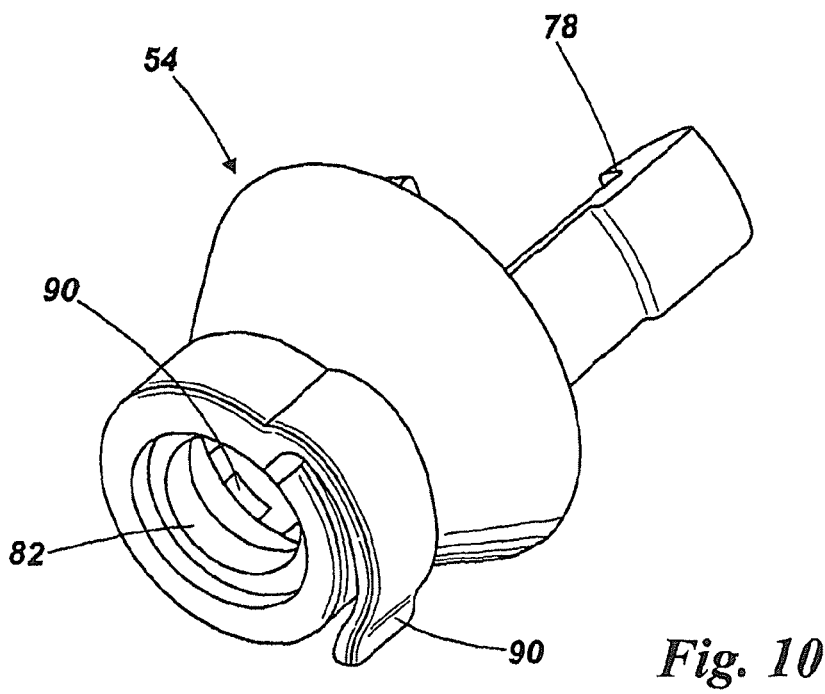
Figure 11:
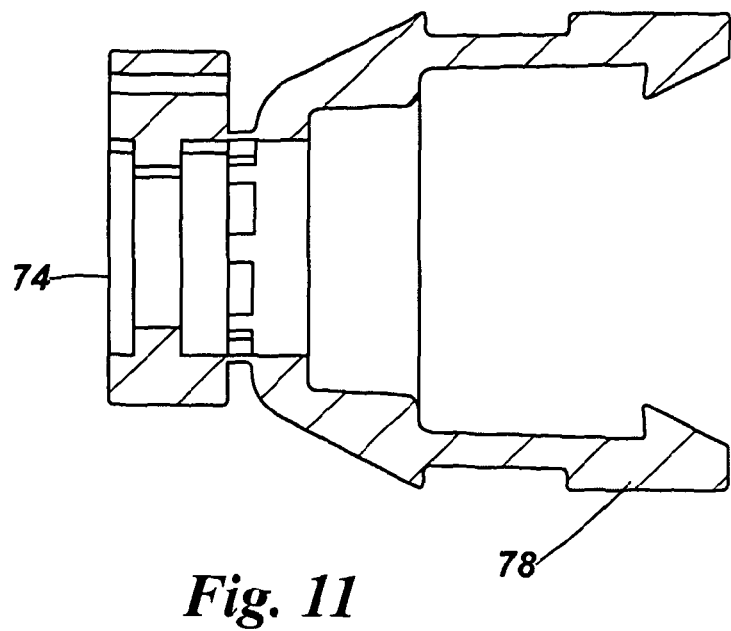
Figure 12:
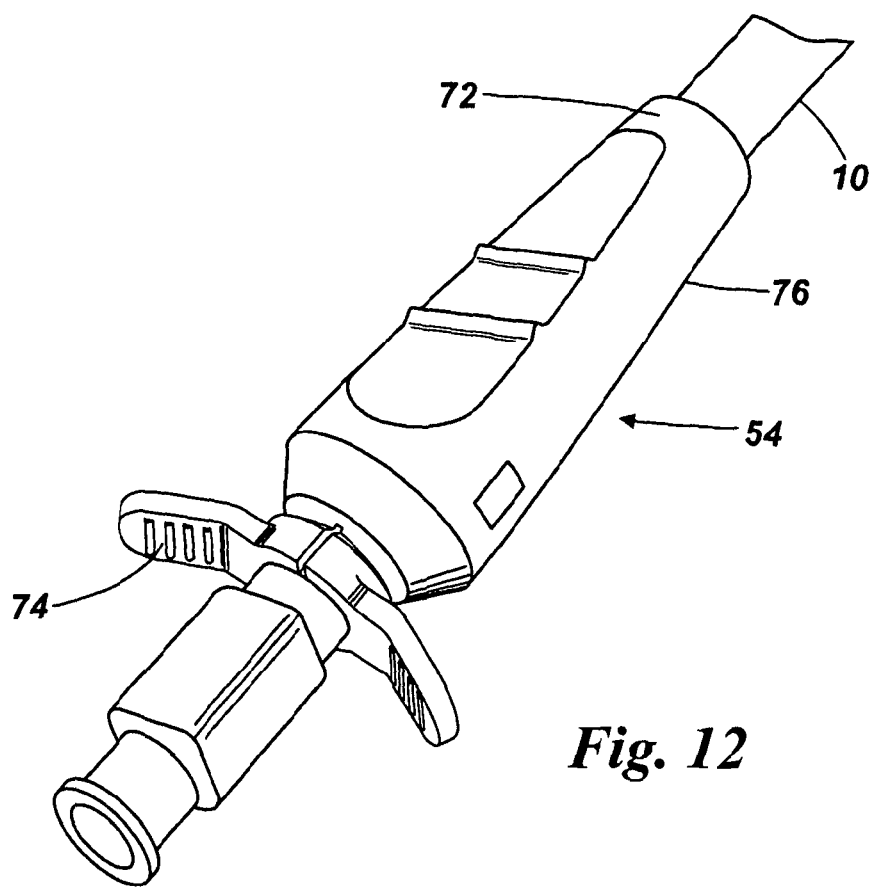
Figure 13:
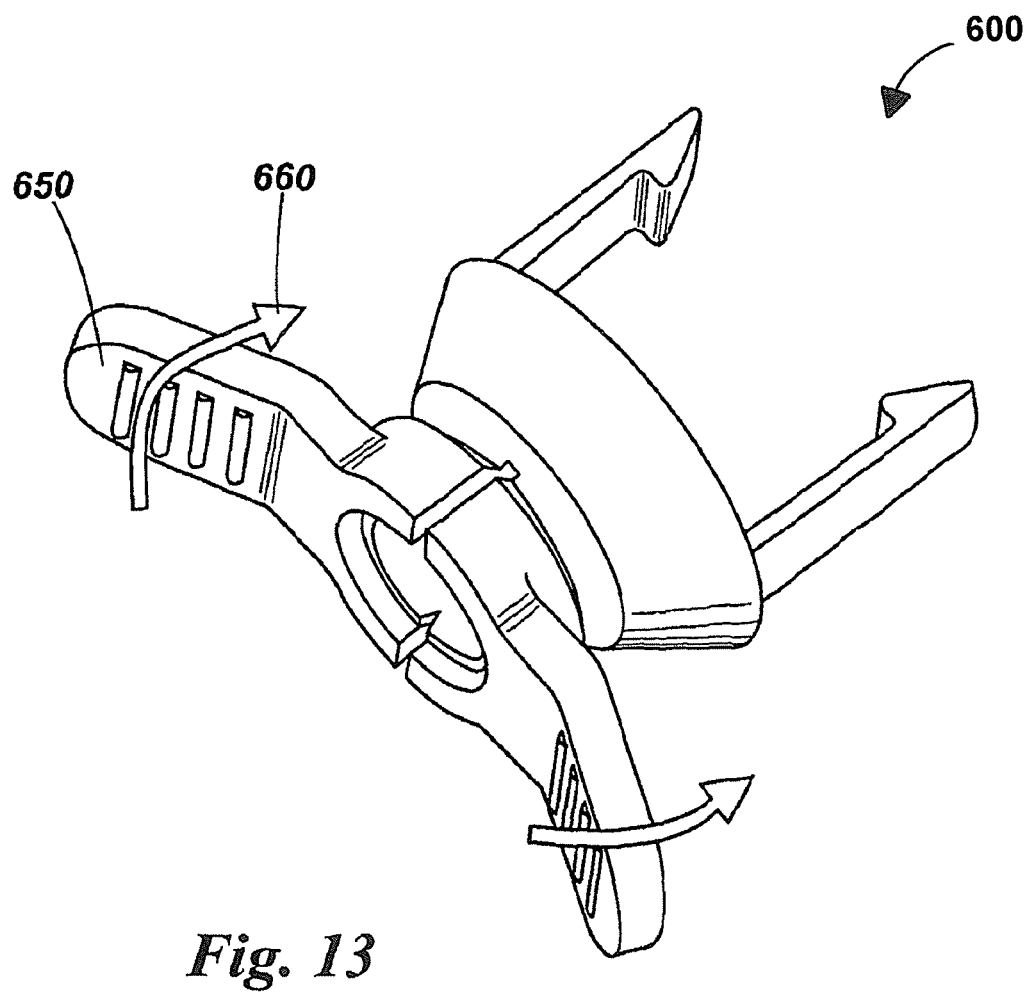

The invention will now be further described by way of example only with reference to the accompanying drawings in which;
  FIG. 1 shows a schematic representation of an outer sleeve of a catheter according to an embodiment of the present invention;
  FIG. 2 shows a side view of an inner sleeve of the catheter of FIG. 1;
  FIG. 3 shows a cross-sectional side view of one end of the catheter of FIGS. 1 and 2 in an assembled and closed configuration;
  FIG. 4 shows a cross-sectional side view of one end of the catheter of FIGS. 1 and 2 in an assembled and standard configuration;
  FIGS. 5 and 6 are schematic representations of a lock mechanism forming part of a catheter according to a first embodiment of the present invention;
  FIG. 7 is a schematic representation of a lock mechanism forming part of a catheter according to a second embodiment of the present invention;
  FIG. 8 is a schematic representation of an adaptor forming part of a locking mechanism of FIG. 7;
  FIG. 9 is a schematic representation of the locking cone forming part of the locking mechanism of FIG. 7;
  FIG. 10 is a schematic representation of a releaser forming part of the lock mechanism of FIG. 7;
  FIG. 11 is a schematic representation of the releaser of FIG. 10;
  FIG. 12 is a schematic representation of the lock mechanism forming part of the catheter according to a third embodiment of the present invention; and
  FIG. 13 is a schematic representation of the releaser forming part of the lock mechanism of FIG. 12.

With reference to FIG. 1, an outer sleeve 10 for a catheter comprises a flexible tube of suitable material such as polymer compounds including PVC or polyurethane, latex, or rubber having an outer diameter suitable for introduction of the catheter into the urethra of a patient's body. The length of the outer sleeve may be any suitable length sufficient to reach from the bladder of a patient to a position external of the body.

The outer sleeve 10 has a proximal end 11 that normally remains outside the patient's body, and a distal end 12 that reaches into the bladder. A plurality of slits 13 are cut through the walls of the outer sleeve to define a deformable zone 14. The deformable zone 14 effectively separates a distal portion 15 and a proximal portion 16 of the outer sleeve 10. The outer sleeve defines a lumen therethrough extending from the proximal end 11 to the distal end 12.

The outer sleeve 10 generally defines a longitudinal axis, but it will be understood that the flexible tube of the outer sleeve allows the outer sleeve to deflect sideways along this axis to assume any necessary curves for entry into and pass through the urethra of the patient. References to the 'axis' of the sleeve herein will generally refer to the centre line of the sleeve regardless of any curvature thereof.

However, the slits 13 in the deformable zone 14 of the outer sleeve 10 allow a further degree of freedom in that the flexible tube is generally axially compressible within the deformable zone. The distal portion 15 and proximal portion 16 may be relatively axially displaced towards one another to effect longitudinal or axial compression such that the tube walls 17 between the slits 13 will splay or bulge outwards to 'open' the slits, as will be described in more detail in connection with FIG. 4.

It will be recognised that to achieve this longitudinal compression, the slits 13 need not be aligned with the longitudinal axis, but merely have a component in that direction. For example, the slits 13 may have a diagonal or spiral alignment, in which case longitudinal compression will still cause the tube walls between the slits to buckle or bulge outwards.

In order to facilitate the desired longitudinal compression of the outer sleeve 10, relative displacement along the longitudinal axis of the distal portion 15 and the proximal portion 16 is required.

As shown in FIG. 2, the catheter further comprises an inner sleeve 20 which extends through the outer sleeve 10. The inner sleeve 20 has a proximal end 21 and a distal end 22 and at least one aperture 23 positioned close to the distal end. More than one aperture 23 may be provided, for example, arranged circumferentially around the inner sleeve 20.

The outside diameter of the inner sleeve 20 is less than the inner diameter of the outer sleeve. The inner sleeve 20 is also formed from a suitable flexible material as indicated above to allow flexing and curving along its longitudinal axis. However, it is preferably sufficiently rigid that compression of the inner sleeve along its longitudinal axis is not possible during normal use.

With reference to FIG. 3, a portion of the assembled catheter 30 is shown in an installation ('closed') configuration, i.e. ready for insertion into a patient. The inner sleeve 20 is contained within the outer sleeve 10 and generally in sliding engagement therewith. However, at the distal ends 22, 12, the inner and outer sleeves 20, 10 are coupled together, using some suitable attachment means comprises a suitable adhesive or other bonding compound 32. Alternatively, any mechanical fixing mechanism could be used to lock the distal ends of inner and outer sleeves together. For example, where the inner and outer sleeves are formed as simple tubes with open ends, a closure device such as a plastic cap may be used to engage both the inner and outer sleeve together while forming a closure of both.

The walls 33 of the outer sleeve 20 between the slits 13 form the deformable part of the catheter 30 and thereby a retainer to be described in detail later.

The aperture 23 of the inner sleeve 20 is generally longitudinally aligned with the slits 13, or possibly slightly displaced towards the distal end, e.g. at least partially into the distal portion 15 of the outer sleeve 10. The reason for this becomes clear with reference to FIG. 4.

In FIG. 4, a portion of the assembled catheter 30 is shown in an installed ('open') configuration, i.e. after insertion into a patient and with the retainer deployed. In this configuration, the inner sleeve 20 has been displaced relative to the outer sleeve 10 in the proximal portion 16, in an axial direction—to the right as shown in the figure. Because the distal portion of the outer sleeve is relatively fixed to the distal end of the inner sleeve 20, the relative displacement of the inner and out sleeves in the proximal portion 16 causes the walls 33 of the outer sleeve to buckle or deform so as to bulge or splay outwardly as shown.

The outward splaying of walls 33 results in the slits 13 opening up into apertures 40 (shown in dashed outline), which apertures are coincident with the underlying aperture or apertures 23 of the inner sleeve 20, as shown. It will be observed that this provides two functions.

Firstly, the splaying of the walls 33 provides a retainer that ensures that the catheter remains in situ within the bladder, the trailing edge 41 of the splayed wall 33 engaging with the neck of the bladder to prevent egress of the distal end past the bladder neck.

Secondly, the splaying of the walls 33 opens up the apertures 40 in the outer sleeve 10 so that fluid communication between the outer surface of the catheter and the lumen 42 of the inner sleeve 20 is possible via the aperture (s) 23. Thus, urine may then drain out of the bladder via the catheter lumen 42.

A particular advantage of this configuration is that the apertures 40, 23 are in very close proximity to the trailing edge 41 of the wall 33 that engages with the neck of the bladder, so that there is very little tendency for pooling of urine near the neck of the bladder.

Preferably, the respective diameters of the inner and outer sleeves 20, 10 are closely matched so that there is a very little gap 43 between the sleeves, while still allowing sliding engagement of the walls of the inner and outer sleeves. Preferably, the gap 43 is sufficiently small that no urine or other liquid can travel the length of the catheter 30 between the walls of the inner and outer sleeves 20, 10.

More preferably, a lubricious coating is applied to the inner surface of the outer sleeve 10 and/or to the outer surface of the inner sleeve 20 to facilitate the relative axial displacement of the inner and outer sleeves. An example of a lubricious coating could be PTFE.

Alternatively, a lubricant may be generally inserted into the gap 43 for similar purposes.

The catheter 30 further comprises a lock mechanism 50 for locking the inner and outer sleeves 20, 10 in a predetermined axial displacement corresponding to the open configuration shown in FIG. 4. The lock mechanism 50 is particularly suitable for use with a catheter in which the walls 33 of the outer sleeve 10 are resilient such that there is a tendency for them to try to close the apertures 40 that have been opened up in the open configuration.

The lock mechanism 50 according to an embodiment of the invention is illustrated in FIG. 5 and comprises a lock 52 having a first lock component 54 formed on the outer sleeve, and a second lock component 56 formed on the inner sleeve. The first and second lock components 54, 56 are engageable with one another when the catheter is in its open position.

In the illustrated embodiment, the first lock component comprises a groove 58 extending circumferentially around an inner surface 60 of the outer sleeve 10. The second lock portion comprises a ridge 62 extending circumferentially and outwardly from an outer surface of the inner sleeve 10.

The lock mechanism further comprises a releaser 64 comprising a frangible portion 65 defined by lines of weakness 66, 68, and a tab 70 extending from an outer surface of the outer sleeve 10.

As explained hereinabove with reference to FIG. 4, after the catheter has been inserted into the patient, the inner sleeve 20 is displaced relative to the outer sleeve 10 in the proximal portion 16 by moving the inner sleeve 10 in the direction of arrow X (FIG. 5). This causes the walls 33 of the outer sleeve to buckle or deform so as to bulge or splay outwardly as shown in FIG. 4, so that the catheter is in the open state.

The first and second lock components, 54, 56 are positioned on the inner and outer sleeves respectively such that when the relative displacement of the inner and outer sleeves reach the desired extent, the first and second lock components 54, 56 will engage with one another and hold the inner and outer sleeves in this position and thus hold the catheter in the open state.

The positioning of the first and second lock portions thus ensures that a clinician installing the catheter 30 achieves the correct or agreed compression of a deformable zone 14.

When it is required to remove the catheter from a patient, a clinician may take hold of the tab 70 and pull it away from the outer sleeve. This will cause the releaser to break along the lines of weakness 66, 68 and will thus remove some or all of the first lock component 54. This has the effect of disengaging the first and second lock components thus allowing the inner and outer sleeves to return to their original closed position. The catheter may then be removed from the patient.

Referring now to FIGS. 7 to 11, a lock mechanism 500 forming part of a catheter according to a second embodiment of the invention will now be described. Parts of the lock mechanism 500 corresponding to parts of the lock mechanism 50 have been given corresponding reference numerals for ease of reference.

The lock mechanism 500 is a lock 52 comprising a first lock component 54 and second lock component 58. In this embodiment the first lock component 54 is formed separately from the outer sleeve 10, and the second lock component 58 is formed separately from the inner sleeve 20.

The first lock component 54 comprises a first lock portion 72 and a second lock portion 74. The first and second lock portions 72, 74 are engageable with one another.

In this embodiment, the first lock portion 72 comprises an adaptor 76 mounted on the outer sleeve 10, and the second lock portion 74 comprises a releaser 64. The releaser 64 is engageable with both the first lock portion of the first lock component, and the second lock component. The releaser 64 comprises clips 78 which are shaped to fit within recesses 80 formed in the adaptor 76. The releaser 64 further comprises a locking rib 82 which is engageable with groove 84 formed on the second lock component.

When it is required to deploy the catheter 30, the inner and outer sleeves 20, 10 are moved longitudinally relative to one another. That has the effect that the inner sleeve 10 passes through the releaser 64 to take up the position shown in FIG. 7. When the locking rib 82 locates in groove 84, the inner sleeve 10 is held in position relative to the outer sleeve 20.

The second lock component comprises a second groove 86 which is engageable with a rib 88 formed in the adaptor 76. When the first and second sleeves are in the position shown in FIG. 7 in which the catheter is in its open state, the rib 88 of the adaptor 76 will be locked in position in the locking groove 86 of the second lock component. This further secures the inner sleeve relative to the outer sleeve.

When it is required to remove the catheter from a patient's body, a clinician may take hold of tab 70 of releaser 64. By pulling the tab the releaser will break along a frangible portion 90, which in this embodiment comprises a plurality of recesses 90 formed in the releaser 64. Once the releaser has been broken in this way, locking rib 82 will no longer be in engagement with the groove 84 of the second lock component. The catheter may therefore return to its closed state and the catheter may be removed from the patient's body.

Turning now to FIGS. 12 and 13, a lock mechanism 600 forming part of a catheter according to a third embodiment of the invention will now be described. Parts of the lock mechanism 600 corresponding to parts of the lock mechanisms 50, 500 have been given corresponding reference numerals for ease of reference.

The components of lock mechanism 600 are similar to those of lock mechanism 500. However, the releaser 64 comprises handles 650 rather than tab 70. In order to break the releaser 64, force may be applied to the handles 650 in the direction of arrows 660. This causes the first lock portion 54 to break thus releasing the engagement between the first lock component 54 and the second lock component 56. The catheter further comprises a female luer 100 as is known in the art.

Although the lock mechanism formed part of an embodiment of the present invention has been described hereinabove with reference to a catheter comprising a retainer in the form of a deformable zone formed at a distal portion of the outer sleeve, it is to be understood that the lock mechanism could form part of any catheter comprising an inner sleeve and an outer sleeve in which it is necessary to longitudinally displace the inner and outer sleeves relative to one another in order to deploy the catheter in its open state.

A catheter according to the present invention may be adapted for both transurethral and suprapubic introduction into the bladder.

In addition, a catheter according to the invention adapted for suprapubic introduction into the bladder, the catheter may be inserted into a housing or valve that is adapted to rest on a patient's stomach. This allows the patient or carer to drain the bladder intermittently.

The invention claimed is:

1. A catheter comprising an inner sleeve and an outer sleeve surrounding the inner sleeve, the inner and the outer sleeves being longitudinally displaceable relative to one another to enable the catheter to move from an open state to a closed state, each sleeve having a distal portion and a proximal portion, the catheter further comprising a retainer which is open in the open state, and closed in the closed state, and a lock mechanism comprising a lock for locking the catheter in the open state, and a releaser for releasing the lock, the releaser comprising a frangible portion of the lock, and is adapted to remove at least a part of the lock from the catheter, wherein the lock comprises a first lock component, and a second lock component, the first and second lock components being engageable with one another when the catheter is in the open state; and wherein the inner sleeve has an aperture positioned close to the distal portion of the inner sleeve, wherein the outer sleeve has a deformable zone having slits, wherein the slits are open in the open state of the catheter, such that urine drains through the slits, then through the aperture of the inner sleeve, and then longitudinally through the inner sleeve, and wherein the slits of the deformable zone of the outer sleeve are closed in the closed state of the catheter.

2. A catheter as claimed in claim 1 wherein the lock is positioned in the proximal portion of the catheter.

3. A catheter as claimed in claim 1 wherein the first lock component is formed on, or attachable to the outer sleeve, and the second lock component is formed on, or attachable to the inner sleeve.

4. A catheter according to claim 1 wherein the first and second lock components are formed from the outer and inner sleeves respectively.

5. A catheter according to claim 1 wherein the second lock component comprises a conical component.

6. A catheter according to claim 1 wherein the first lock component comprises a first lock portion adapted to engage with the outer sleeve, and a second lock portion adapted to engage with the first lock portion.

7. A catheter as claimed in claim 6 wherein the first lock portion comprises an adaptor engageable with the outer sleeve.

8. A catheter as claimed in claim 6 wherein the second lock portion is engageable with the second lock component.

9. A catheter as claimed in claim 6 wherein the second lock portion comprises the releaser.

10. A catheter as claimed in claim 1 wherein the first lock component comprises a groove extending substantially circumferentially around an inner surface of the outer sleeve, and the second lock component comprises a ridge extending substantially circumferentially around an outer surface of the inner sleeve.

11. A catheter comprising an inner sleeve and an outer sleeve surrounding the inner sleeve, the inner and outer sleeves being longitudinally displaceable relative to one another to enable the catheter to move from an open state to a closed state, each sleeve having a distal portion and a proximal portion, the catheter further comprising a retainer which is open in the open state, and closed in the closed state, and a lock mechanism comprising a lock for locking the catheter in the open state, and a releaser for releasing the lock, the releaser being adapted to remove at least a part of the lock from the catheter;

wherein the lock comprises a first lock component, and a second lock component, the first and second lock components being engageable with one another when the catheter is in the open state, the first lock component comprising a first lock portion adapted to engage with the outer sleeve, and a second lock portion adapted to engage with the first lock portion, and wherein the second lock portion comprises the releaser, which releaser comprises a frangible portion; and wherein the inner sleeve has an aperture positioned close to the distal portion of the inner sleeve, wherein the outer sleeve has a deformable zone having slits, wherein the slits are open in the open state of the catheter, such that urine drains through the slits, then through the aperture of the inner sleeve, and then longitudinally through the inner sleeve, and wherein the slits of the deformable zone of the outer sleeve are closed in the closed state of the catheter.

* * * * *